(12) United States Patent
Matsubara

(10) Patent No.: US 11,397,313 B2
(45) Date of Patent: Jul. 26, 2022

(54) OBSERVATION APPARATUS, OBSERVATION METHOD, AND OBSERVATION PROGRAM

(71) Applicant: FUJIFILM Corporation, Tokyo (JP)

(72) Inventor: Kenta Matsubara, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 272 days.

(21) Appl. No.: 16/798,636

(22) Filed: Feb. 24, 2020

(65) Prior Publication Data

US 2020/0257102 A1  Aug. 13, 2020

Related U.S. Application Data

(63) Continuation of application No. PCT/JP2018/033019, filed on Sep. 6, 2018.

(30) Foreign Application Priority Data

Sep. 29, 2017  (JP) .............................. JP2017-191004

(51) Int. Cl.
G02B 21/02    (2006.01)
G02B 21/24    (2006.01)
G02B 21/36    (2006.01)

(52) U.S. Cl.
CPC ........... *G02B 21/245* (2013.01); *G02B 21/36* (2013.01)

(58) Field of Classification Search
CPC .............................. G02B 21/245; G02B 21/36
(Continued)

(56) References Cited

U.S. PATENT DOCUMENTS

2007/0229797 A1   10/2007  Sugimoto
2009/0317895 A1   12/2009  Kiyota
(Continued)

FOREIGN PATENT DOCUMENTS

JP    2007263926 A    10/2007
JP    2015166829 A    9/2015
(Continued)

OTHER PUBLICATIONS

The extended European search report issued by the European Patent Office dated Oct. 19, 2020, which corresponds to European Patent Application No. 18862222.9-1020 and is related to U.S. Appl. No. 16/798,636.

(Continued)

*Primary Examiner* — William Choi
(74) *Attorney, Agent, or Firm* — Studebaker & Brackett PC

(57) ABSTRACT

An observation apparatus, an observation method, and an observation program capable of capturing an image by appropriately adjusting a focus regardless of a size of an effective range in which a distance to a cultivation container can be measured within a field of view are provided. An observation apparatus includes an imaging unit 37 that images an observation target in a field of view smaller than an accommodation part 22 at a series of imaging positions and acquires a series of partial images, a measurement unit 38 that measures a distance from the imaging unit 37 to the accommodation part 22, a storage unit 44 that stores shape information of a container 20 and a series of imaging position information, a calculation unit 45 that calculates effective range information indicating an effective range in which the measurement unit 38 is capable of performing measurement before imaging within a field of view of the imaging unit 37 at the imaging positions, based on the shape (Continued)

information and the imaging position information, and a control unit 40 that controls a focus of the imaging unit 37 using a measurement result measured by the measurement unit 38 in the effective range and a measurement result of the measurement unit 38 in a field of view adjacent to the field of view including the effective range in a case where the effective range is smaller than or equal to a threshold value.

5 Claims, 7 Drawing Sheets

(58) Field of Classification Search
    USPC .......................................................... 359/656
    See application file for complete search history.

(56) References Cited

U.S. PATENT DOCUMENTS

| 2012/0120302 | A1 | 5/2012 | Kiyota et al. |
| 2014/0210981 | A1 | 7/2014 | Stauffer |
| 2014/0247379 | A1 | 9/2014 | Najmabadi et al. |
| 2014/0313312 | A1 | 10/2014 | Gaiduk et al. |
| 2015/0124082 | A1 | 5/2015 | Kato et al. |
| 2015/0358533 | A1 | 12/2015 | Tanaka |
| 2016/0369223 | A1 | 12/2016 | Matsumoto |
| 2017/0237894 | A1 | 8/2017 | Hikida |
| 2017/0257538 | A1 | 9/2017 | Kokubo |
| 2017/0322405 | A1 | 11/2017 | Matsubara |

FOREIGN PATENT DOCUMENTS

| JP | 2016099592 A | 5/2016 |
| JP | 2016149998 A | 8/2016 |
| JP | 2017143759 A | 8/2017 |
| WO | 2008146474 A1 | 12/2008 |
| WO | 2014030378 A1 | 2/2014 |
| WO | 2016/084551 A1 | 6/2016 |
| WO | 2016/116897 A1 | 7/2016 |

OTHER PUBLICATIONS

International Search Report issued in PCT/JP2018/033019; dated Nov. 27, 2018.
International Preliminary Report on Patentability and Written Opinion issued in PCT/JP2018/033019; dated Mar. 31, 2020.

MOVEMENT DIRECTION
(FORWARD PATH)

OBSERVATION APPARATUS, OBSERVATION METHOD, AND OBSERVATION PROGRAM

CROSS-REFERENCE TO RELATED APPLICATIONS

This application is a Continuation of PCT International Application No. PCT/JP2018/033019 filed on Sep. 6, 2018, which claims priority under 35 U.S.C § 119(a) to Japanese Patent Application No. 2017-191004 filed on Sep. 29, 2017. Each of the above application(s) is hereby expressly incorporated by reference, in its entirety, into the present application.

BACKGROUND OF THE INVENTION

1. Field of the Invention

The technology of the disclosure relates to an observation apparatus, an observation method, and an observation program for observing an observation target by relatively moving at least one of a container accommodating the observation target or an imaging unit with respect to the other.

2. Description of the Related Art

In recent years, various technologies for imaging an observation target such as various cells and analyzing an acquired image have been suggested. For example, a method of imaging a pluripotent stem cell such as an embryonic stem (ES) cell and an induced pluripotent stem (iPS) cell, a differentiation-induced cell, or the like using a microscope and determining a differentiation state or the like of the cell by recognizing a feature of the image has been suggested. For example, JP2016-149998A discloses an identification apparatus that can suitably specify an observation target even in a case where an imaging condition or the like changes. In addition, JP2016-099592A discloses a microscope that adjusts refraction of illumination light caused by a liquid surface shape of a solution for culturing a cell. In addition, WO2008/146474A discloses an observation apparatus that can recognize an amount of a culture medium for culturing a cell.

The pluripotent stem cell such as the ES cell and the iPS cell has a capability to differentiate into cells of various tissues and has drawn attention for its applicability in regenerative medicine, development of medication, identification of diseases, and the like.

In a case where the cell is imaged as described above, it is known that the cell as the observation target is scanned and measured by the microscope and is determined from an obtained image. In order to implement industrialization of regenerative medicine or multilevel experiment in drug discovery research, it is important to perform imaging at a high speed and determine quality at a high speed.

In a case where a cell that is cultured using a cultivation container such as a well plate, a Petri dish, and a flask is observed, an imaging position (for example, coordinates) at which scanning and measurement are performed is decided in accordance with a shape and a dimension of the cultivation container. The microscope is moved along a scanning trajectory that passes through the decided imaging position.

SUMMARY OF THE INVENTION

Even in a case where imaging is performed along the decided scanning trajectory, an unintended image may be captured. For example, in a case where a distance to the cultivation container is measured by a laser displacement meter before imaging and a focal length at the imaging position is specified based on a measurement result, the measurement result of the laser displacement meter may not be obtained in a range sufficient for specifying the focal length. Specifically, in a case where a field of view of the microscope is smaller than an accommodation part that accommodates the cell or the like in the cultivation container, a center of the accommodation part is not imaged, and an end of the accommodation part is imaged depending on the imaging position. Before the imaging of the end of the accommodation part, the end of the accommodation part that enters the field of view is measured by the laser displacement meter that is present before the end of the accommodation part. However, in a case where only the end of the accommodation part enters the field of view, a range (effective range) of the accommodation part that can be measured by the laser displacement meter within the field of view is narrower than the effective range in a case where the accommodation part enters most of the field of view. In a case where the effective range is narrow, the measurement result is significantly affected by disturbance when disturbance such as vibration occurs within the effective range. In a case where a focus is adjusted based on the measurement result significantly affected by disturbance, the focus may deviate from the cell or the like, and an unintended image may be captured.

The technology of the disclosure is conceived in view of the above point. An object of the technology of the disclosure is to provide an observation apparatus, an observation method, and an observation program capable of capturing an image by appropriately adjusting a focus regardless of a size of an effective range in which a distance to a cultivation container can be measured within a field of view.

An observation apparatus according to the technology of the disclosure comprises an imaging unit that images an observation target accommodated in an accommodation part of a container in a field of view smaller than the accommodation part at a series of predetermined imaging positions and acquires a series of partial images, a measurement unit that measures a distance from the imaging unit to the accommodation part before each imaging performed by the imaging unit at the series of imaging positions, a storage unit that stores shape information representing a shape of the container and imaging position information representing the series of imaging positions, a calculation unit that calculates effective range information indicating an effective range based on the shape information and the imaging position information, the effective range being a range in which the distance is measurable by the measurement unit before imaging within a range of the field of view of the imaging unit at the imaging positions, and a control unit that compares the effective range with a predetermined threshold value based on the effective range information and controls a focus of imaging using a measurement result measured by the measurement unit in the effective range and a measurement result of the measurement unit in a field of view adjacent to the field of view including the effective range in a case where the effective range is smaller than or equal to the threshold value.

The partial image is an image that is obtained by imaging by the imaging unit in a field of view of the imaging unit at each of a plurality of predetermined imaging positions. The shape information is information that is acquired in advance before capturing of the partial image, and is, for example, information representing a size of the accommodation part and a position of the accommodation part in the entire container. The effective range is a range in a scanning direction of the measurement unit and is a range in which the measurement unit can measure the distance from the imaging unit to the accommodation part within the range of the field of view at a time of imaging by the imaging unit from the imaging position. For example, the effective range information as information indicating the effective range indicates coordinate information of the effective range in a movement direction of the measurement unit or a length of the effective range in the movement direction of the measurement unit calculated from the coordinate information. The predetermined threshold value is a value that can be randomly decided by a user and, for example, is set to a length, in a movement direction of the imaging unit, of a range in which desired accuracy is secured even with disturbance as a scanning range in which the measurement unit measures the distance to the accommodation part.

In the observation apparatus, in a case where the effective range is smaller than or equal to the threshold value, the control unit may use the measurement result of the measurement unit in the adjacent field of view in a larger range as the effective range is smaller.

In the observation apparatus, the threshold value may be a length of half of a width of the field of view of the imaging unit.

In the observation apparatus, in a case where the effective range is smaller than or equal to the threshold value, the control unit may control the focus using the measurement result of the measurement unit in the adjacent field of view to an extent of an insufficient length of the effective range with respect to the threshold value.

An observation method according to the technology of the disclosure comprises a measurement step of, in a case where an observation target accommodated in an accommodation part of a container is imaged by an imaging unit having a field of view smaller than the accommodation part at a series of predetermined imaging positions and a series of partial images are acquired, measuring a distance from the imaging unit to the accommodation part before acquisition of each of the series of partial images, a storage step of storing shape information representing a shape of the container and imaging position information representing the series of imaging positions, a calculation step of calculating effective range information indicating an effective range based on the shape information and the imaging position information, the effective range being a range in which the distance is measurable in the measurement step before imaging within a range of the field of view at the imaging positions, and a control step of comparing the effective range with a predetermined threshold value based on the effective range information calculated in the calculation step and controlling a focus of imaging using a measurement result measured in the measurement step in the effective range and a measurement result of the measurement step in a field of view adjacent to the field of view including the effective range in a case where the effective range is smaller than or equal to the threshold value.

An observation program according to the technology of the disclosure causes a computer to execute a measurement step of, in a case where an observation target accommodated in an accommodation part of a container is imaged by an imaging unit having a field of view smaller than the accommodation part at a series of predetermined imaging positions and a series of partial images are acquired, measuring a distance from the imaging unit to the accommodation part before acquisition of each of the series of partial images, a storage step of storing shape information representing a shape of the container and imaging position information representing the series of imaging positions, a calculation step of calculating effective range information indicating an effective range based on the shape information and the imaging position information, the effective range being a range in which the distance is measurable in the measurement step before imaging within a range of the field of view at the imaging positions, and a control step of comparing the effective range with a predetermined threshold value based on the effective range information calculated in the calculation step and controlling a focus of imaging using a measurement result measured in the measurement step in the effective range and a measurement result of the measurement step in a field of view adjacent to the field of view including the effective range in a case where the effective range is smaller than or equal to the threshold value.

Another observation apparatus according to the technology of the disclosure comprises a memory that stores an instruction to be executed by a computer, and a processor configured to execute the stored instruction. The processor executes a measurement step of, in a case where an observation target accommodated in an accommodation part of a container is imaged by an imaging unit having a field of view smaller than the accommodation part at a series of predetermined imaging positions and a series of partial images are acquired, measuring a distance from the imaging unit to the accommodation part before acquisition of each of the series of partial images, a storage step of storing shape information representing a shape of the container and imaging position information representing the series of imaging positions, a calculation step of calculating effective range information indicating an effective range based on the shape information and the imaging position information, the effective range being a range in which the distance is measurable in the measurement step before imaging within a range of the field of view at the imaging positions, and a control step of comparing the effective range with a predetermined threshold value based on the effective range information calculated in the calculation step and controlling a focus of imaging using a measurement result measured in the measurement step in the effective range and a measurement result of the measurement step in a field of view adjacent to the field of view including the effective range in a case where the effective range is smaller than or equal to the threshold value.

According to the technology of the disclosure, in a case where the effective range in which the measurement unit can perform measurement before imaging within the range of the field of view is smaller than or equal to the threshold value, the focus is controlled using the measurement result in the effective range and also the measurement result of the measurement unit in the adjacent field of view. Accordingly, an image can be captured by appropriately adjusting the focus regardless of the size of the effective range in which the distance to the cultivation container can be measured within the field of view.

DESCRIPTION OF THE PREFERRED EMBODIMENTS

Figure 1:
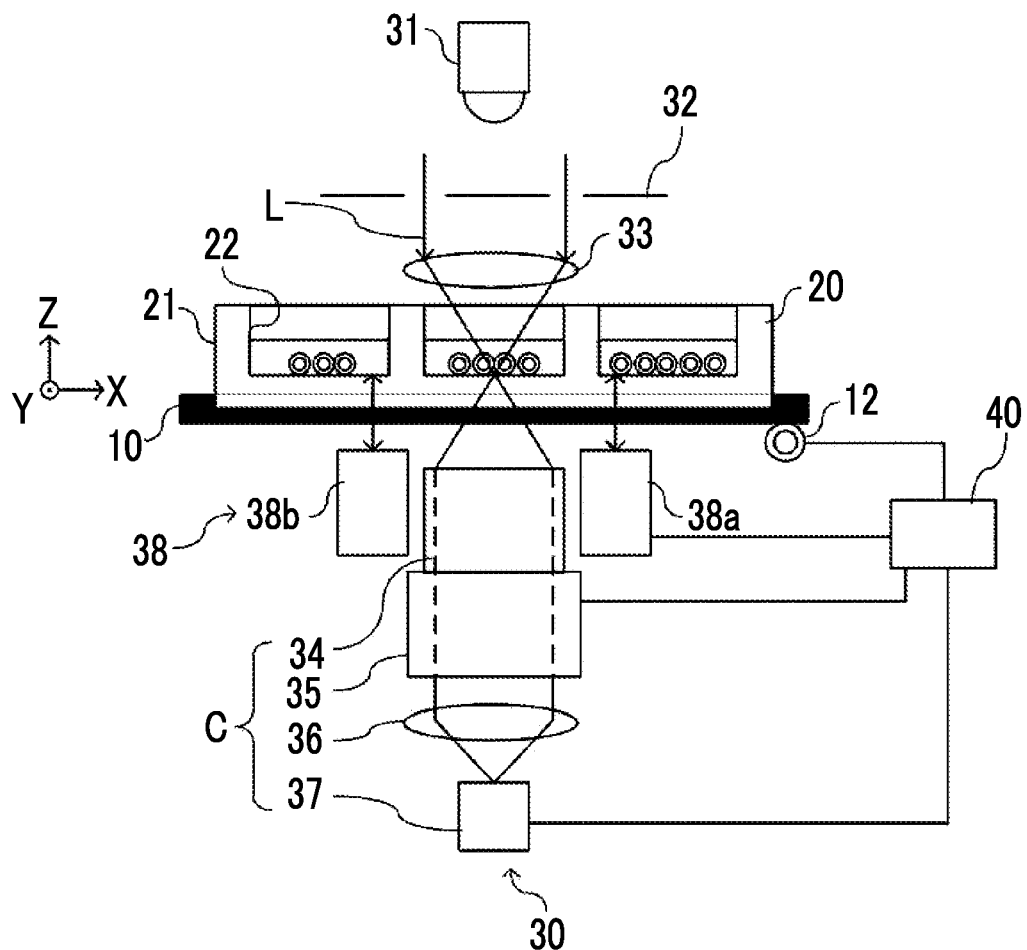
FIG. 1 is a diagram illustrating a schematic configuration of an observation apparatus according to an embodiment of the technology of the disclosure.

Hereinafter, one example of an embodiment according to the technology of the disclosure will be described with reference to the drawings. The same or equivalent constituents and parts in each drawing will be designated by the same reference signs. Dimensional ratios in the drawings are exaggerated for convenience of description and may be different from the actual ratios.

Figure 2:
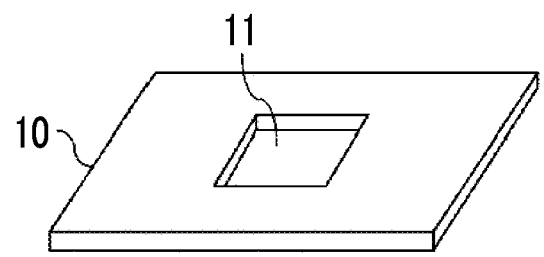
FIG. 2 is a diagram illustrating one example of a placing stand.

FIG. 1 is a diagram illustrating a schematic configuration of an observation apparatus according to the embodiment of the technology of the disclosure. FIG. 2 is a diagram illustrating one example of a placing stand.

The observation apparatus is an apparatus for observing an observation target accommodated in a cultivation container 20 placed on a placing stand 10 by a microscope device 30. The placing stand 10 and the microscope device 30 are controlled by a control unit 40. Each configuration will be described in order.

The placing stand 10 is a stage on which the cultivation container 20 can be placed. As illustrated in FIG. 2, a rectangular opening 11 is formed at the center of the placing stand 10. It is configured that the cultivation container 20 is installed on a member forming the opening 11, and light for observation by the microscope device 30 passes through the cultivation container 20.

A movement unit 12 is attached to the placing stand 10. The movement unit 12 can freely move the placing stand 10 in an X direction and a Y direction that are orthogonal to each other. The X direction and the Y direction are directions orthogonal to a Z direction and are directions orthogonal to each other in a horizontal plane. In the present embodiment, the X direction is set as a main scanning direction, and the Y direction is set as a sub-scanning direction. The movement unit 12 is configured with an actuator that includes a piezoelectric element or the like. Movement of the placing stand 10 in an X-Y plane is controlled by the control unit 40. By moving the placing stand 10 in the X-Y plane, the cultivation container 20 on the placing stand 10 moves with respect to the microscope device 30.

In the present embodiment, an example in which a position at which the observation target is observed by the microscope device 30 is changed by moving the placing stand 10 with respect to the microscope device 30 is illustrated. However, the example is not for limitation purposes. The microscope device 30 may be moved with respect to the placing stand 10, or both of the placing stand 10 and the microscope device 30 may be moved. Any aspect can be employed as long as at least one of the cultivation container 20 placed on the placing stand 10 or the microscope device 30 is relatively moved with respect to the other. In the present disclosure, for example, the "microscope device 30 is represented as relatively moving with respect to the cultivation container 20" even in a case where a position of the microscope device 30 is fixed and only the cultivation container 20 is moving. In addition, in the present disclosure, a trajectory accompanied by the relative movement is represented as a "scanning trajectory" even in a case where any of the microscope device 30 and the cultivation container 20 is actually moving.

Instead of placing the cultivation container 20 on the placing stand 10 and moving the cultivation container 20, the cultivation container 20 may be moved in the X-Y plane using a holding unit that holds at least a part of the cultivation container 20 by moving the holding unit.

In the cultivation container 20, a plurality of accommodation parts 22 are formed in a plate 21 having a flat plate shape. For example, a Petri dish, a dish, or a well plate can be used as the cultivation container 20. For example, the accommodation part 22 is a recessed portion having a circular shape in a plan view and is referred to as a well. The accommodation part 22 accommodates the observation target such as various cells immersed in a cultivation liquid. Cells accommodated in the accommodation part 22 include pluripotent stem cells such as an iPS cell and an ES cell, cells of a nerve, skin, cardiac muscle, and a liver that are differentiation-induced from a stem cell, cells of skin, a retina, cardiac muscle, a blood cell, a nerve, and an organ extracted from a human body, and the like.

The microscope device 30 captures a phase difference image of the observation target. In order to obtain a high magnification image, the microscope device 30 captures partial images of the observation target and the cultivation container 20 in a field of view smaller than each accommodation part 22 of the cultivation container 20. As described above, by moving the cultivation container 20 with respect to the microscope device 30, the microscope device 30 scans the cultivation container 20, and a series of partial images is obtained. The partial image is an image that is obtained by imaging by the microscope device 30 in a field of view of the microscope device 30 at each of a plurality of predetermined imaging positions.

The microscope device 30 comprises a light source 31, a slit 32, a condenser lens 33, an objective lens 34, a focus adjustment mechanism 35, an image forming lens 36, an imaging unit 37, and a measurement unit 38.

The light source 31 emits white light. The slit 32 is formed by disposing a ring shaped slit through which the white light is transmitted in a light screen that blocks the white light emitted from the light source 31. Illumination light L having a ring shape is formed by causing the white light to pass through the slit. The condenser lens 33 condenses the illumination light L having the ring shape on the observation target.

The objective lens 34 is arranged to face the condenser lens 33 through the cultivation container 20. The objective lens 34 forms an image of the observation target in the cultivation container 20. The focus adjustment mechanism 35 includes a phase difference lens that can be moved in an optical axis direction (Z direction). By moving the phase difference lens in the optical axis direction, autofocus control is performed, and contrast of the phase difference image captured by the imaging unit 37 is adjusted. For example, the movement of the phase difference lens in the optical axis direction can be implemented by driving an actuator such as a piezoelectric element based on a signal from the control unit 40. However, the piezoelectric element is not for limitation purposes, and the phase difference lens can be driven using other known configurations as long as the phase difference lens can be moved in the Z direction. In addition, a magnification of the phase difference lens may be configured to be changeable. Specifically, a phase difference lens or the focus adjustment mechanism 35 having a different magnification may be configured to be replaceable. The replacement may be automatically performed or may be manually performed by a user.

The phase difference image that passes through the focus adjustment mechanism 35 is incident on the image forming lens 36, and the image forming lens 36 forms the phase difference image on the imaging unit 37.

The imaging unit 37 is fixedly attached to the measurement unit 38 and captures the phase difference image formed by the image forming lens 36. For example, the imaging unit 37 is an imaging element such as a charge-coupled device (CCD) image sensor or a complementary metal-oxide semiconductor (CMOS) image sensor. As the imaging element, an imaging element in which color filters of red, green, blue (RGB) are disposed may be used, or a monochrome imaging element may be used.

Hereinafter, the objective lens 34, the focus adjustment mechanism 35, the image forming lens 36, and the imaging unit 37 will be collectively referred to as an image forming optical system C.

The measurement unit 38 consecutively detects a Z-directional position of the cultivation container 20 installed on the placing stand 10 along the scanning trajectory accompanied by the relative movement of at least one of the cultivation container 20 or the imaging unit 37.

Specifically, the measurement unit 38 comprises a first displacement sensor 38a and a second displacement sensor 38b. The first displacement sensor 38a and the second displacement sensor 38b are arranged in the X direction illustrated in FIG. 1 with the image forming optical system C interposed therebetween. The first displacement sensor 38a and the second displacement sensor 38b in the present embodiment are laser displacement meters and detect a Z-directional position of a bottom surface of the accommodation part 22 of the cultivation container 20 by irradiating the cultivation container 20 with laser light and detecting reflected light, and measures a distance from the imaging unit 37 to the bottom surface of the accommodation part 22. The bottom surface of the accommodation part 22 is a boundary surface between a bottom portion of the accommodation part 22 and the cell which is the observation target, that is, an observation target installation surface.

The distance detected by the measurement unit 38 from the imaging unit 37 to the bottom surface of the accommodation part 22 is output to the control unit 40. The control unit 40 performs the autofocus control (focus control) by controlling the focus adjustment mechanism 35 based on the input distance. The detection of the position of the cultivation container 20 by the first displacement sensor 38a and the second displacement sensor 38b, and the autofocus control will be described in detail later.

Figure 3:
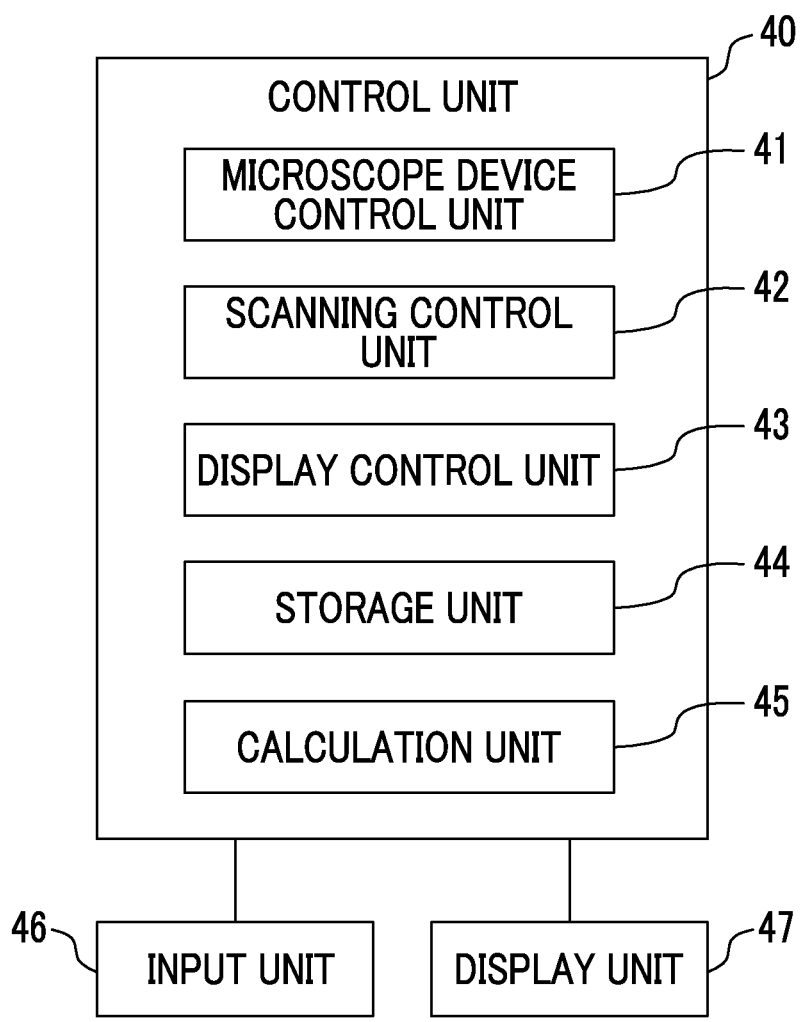
FIG. 3 is a block diagram illustrating a configuration of a control unit according to the embodiment of the technology of the disclosure.

Next, a configuration of the control unit 40 controlling the microscope device 30 will be described. FIG. 3 is a block diagram illustrating a configuration of the control unit according to the embodiment of the technology of the disclosure.

The control unit 40 controls the entire microscope device 30 as described above and executes various processes. The control unit 40 includes a microscope device control unit 41, a scanning control unit 42, a display control unit 43, a storage unit 44, a calculation unit 45, an input unit 46, and a display unit 47. The control unit 40 is configured with a computer that comprises a central processing unit (CPU), a semiconductor memory, and the like. In the control unit 40, an observation program according to one embodiment of the present invention is installed in the storage unit 44. The microscope device control unit 41, the scanning control unit 42, the display control unit 43, and the calculation unit 45 illustrated in FIG. 3 function by causing the CPU to execute the observation program.

The microscope device control unit 41 controls the focus adjustment mechanism 35 based on the distance detected by the measurement unit 38 from the imaging unit 37 to the bottom surface of the accommodation part 22 as described above. By driving the focus adjustment mechanism 35, the phase difference lens moves in the optical axis direction, and the autofocus control is performed.

In addition, the microscope device control unit 41 controls imaging performed by the imaging unit 37 in a case where the cultivation container 20 is scanned. Basically, a timing of imaging during scanning is stored in advance in the storage unit 44. The microscope device control unit 41 performs imaging based on the stored timing.

The scanning control unit 42 controls driving of the movement unit 12 and moves the placing stand 10 in the X direction and the Y direction.

The display control unit 43 generates one composite image by combining the series of partial images captured by the microscope device 30 and displays the composite image on the display unit 47.

The storage unit 44 stores the observation program that implements each function unit. In addition, the storage unit 44 stores shape information of the cultivation container 20 corresponding to container information of the cultivation container 20. For example, the container information of the cultivation container 20 includes specifications (a size, a number, intervals, and the like of accommodation parts 22) of the cultivation container and a model number, a maker, and the like of the cultivation container. The shape information of the cultivation container 20 is information such as the number (6, 24, 96, or the like) of accommodation parts 22 of the cultivation container 20, the intervals of the accommodation parts 22, a diameter of the accommodation part 22, a thickness of the accommodation part 22, and a position of the accommodation part 22 in the cultivation container 20. The shape information may be information of the specifications of the cultivation container 20 published from a manufacturing maker or the like or may be information of a solid shape of the cultivation container 20 obtained by measurement in advance by a shape measurement device such as a laser length measurement device.

Trajectory information indicating the scanning trajectory of the microscope device 30 and imaging position information indicating a series of imaging positions (coordinates) are decided by the scanning control unit 42 based on the container information or the shape information including information of the solid shape of the cultivation container 20, and are stored in the storage unit 44.

Based on the shape information and the imaging position information stored in the storage unit 44, the calculation unit 45 calculates effective range information indicating an effective range that is a range in which the measurement unit 38 can perform measurement before imaging within a range of a field of view of the imaging unit 37 at the imaging position. The effective range is a range in a scanning direction of the measurement unit 38 and is a range in which the measurement unit 38 can measure the distance from the imaging unit 37 to the bottom surface of the accommodation part 22 within the range of the field of view at a time of imaging by the imaging unit 37 from the imaging position. As will be described later, the measurement unit 38 can relatively move before the imaging unit 37 and measure the effective range until the imaging unit 37 reaches the imaging position. For example, the effective range information as information indicating the effective range is coordinate information indicating the effective range in a movement direction of the imaging unit 37 or a length of the effective range in a movement direction of the measurement unit calculated from the coordinate information.

The input unit 46 comprises a mouse, a keyboard, and the like and receives various necessary data and various setting inputs from the user. For example, the input unit 46 of the present embodiment receives an input of data related to the container information of the cultivation container 20 and the imaging positions.

The display unit 47 comprises, for example, a liquid crystal display and displays a composite phase difference image generated by the display control unit 43 as described above. The display unit 47 may be configured with a touch panel and double as the input unit 46.

Next, movement control of the placing stand 10 by the scanning control unit 42 and control of the microscope device 30 by the microscope device control unit 41 will be described in detail.

Figure 4:
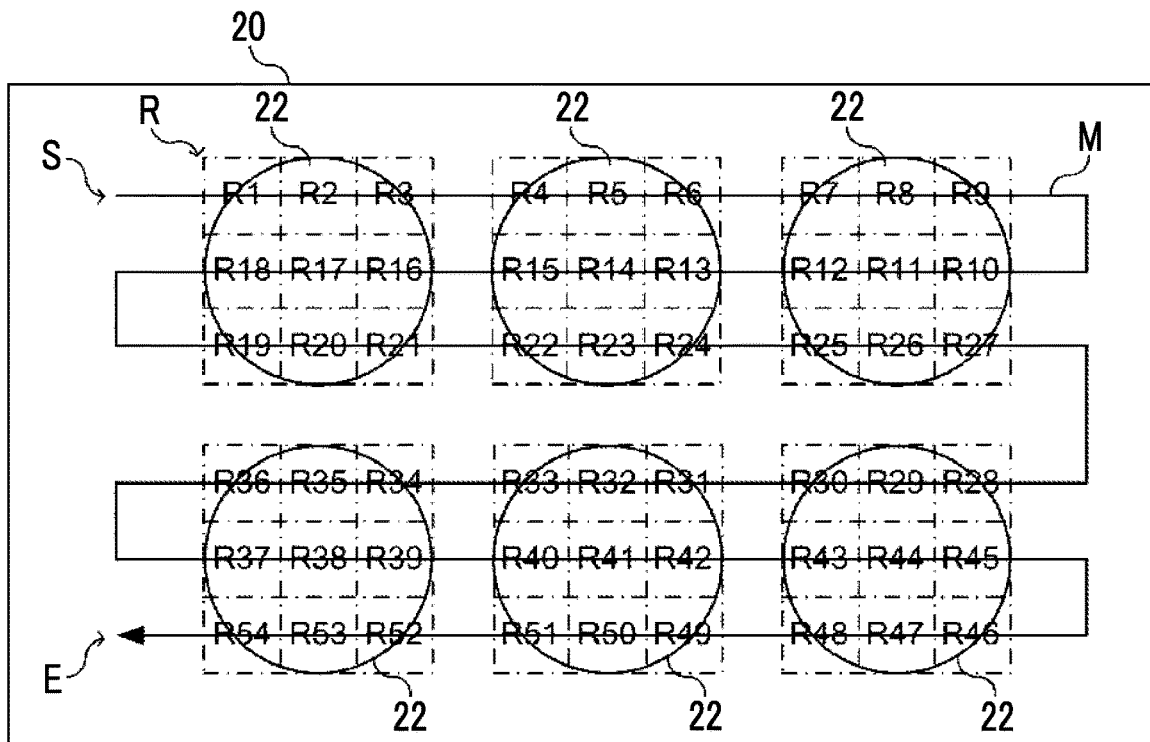
FIG. 4 is a diagram illustrating a scanning trajectory by a solid line M in a cultivation container.
Figure 5:
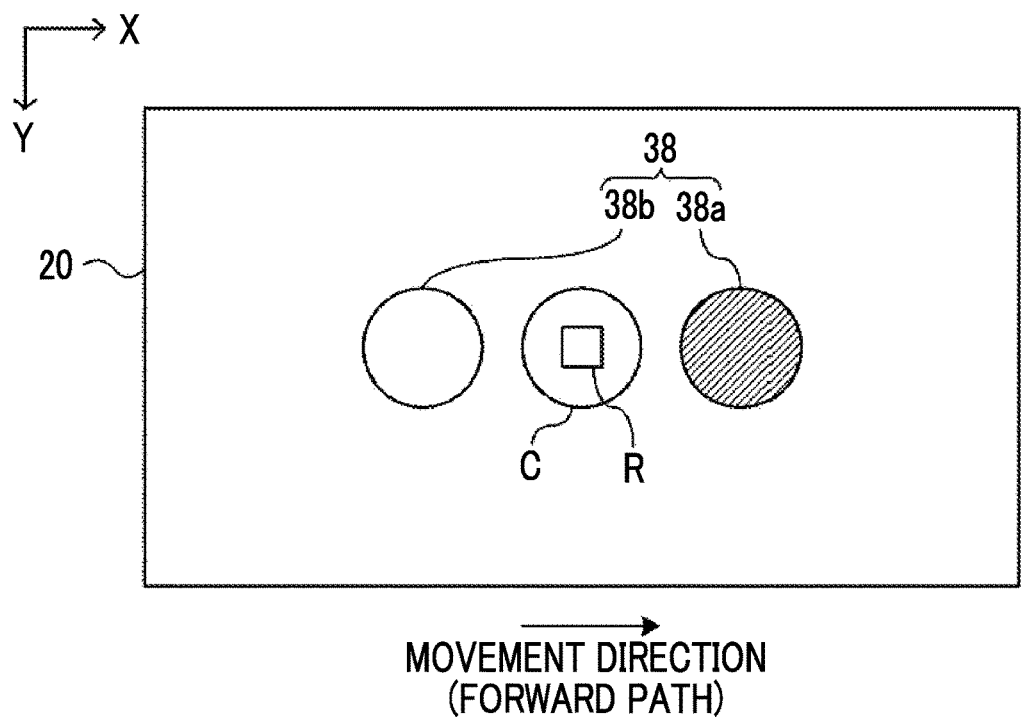
FIG. 5 is a diagram illustrating a positional relationship among a first displacement sensor, a second displacement sensor, and the cultivation container in a case where a field of view is present at any position in the cultivation container.
Figure 6:
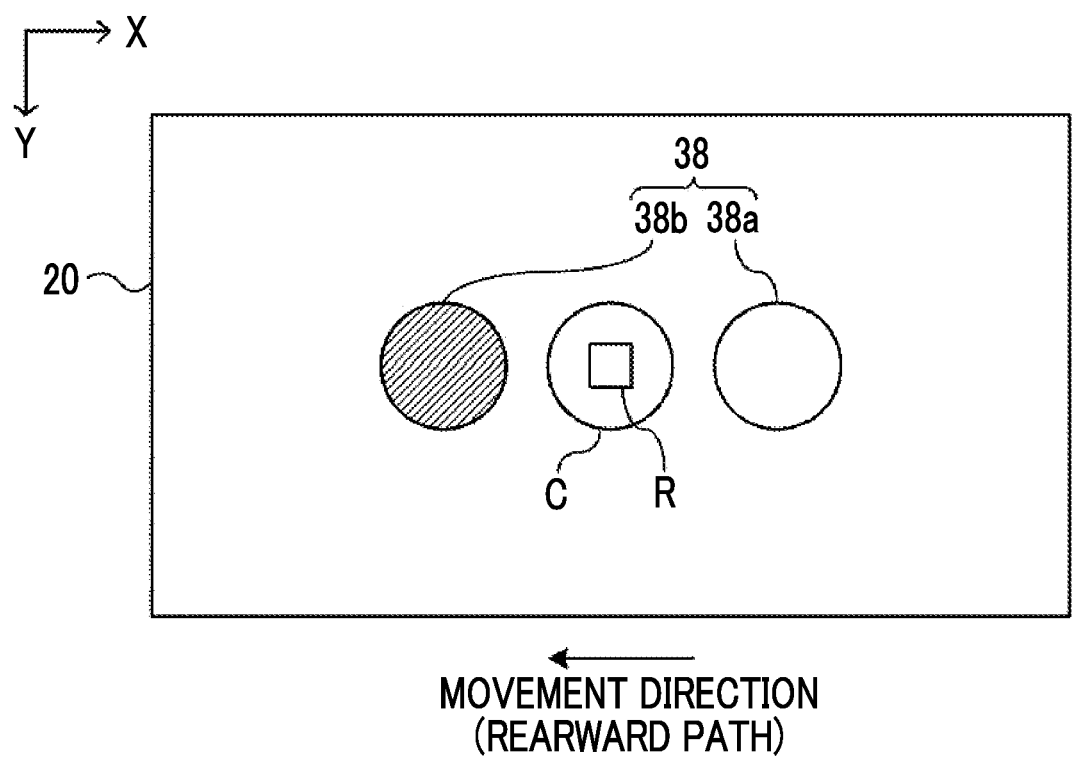
FIG. 6 is a diagram illustrating a positional relationship among the first displacement sensor, the second displacement sensor, and the cultivation container in a case where the field of view is present at any position in the cultivation container.
Figure 7:
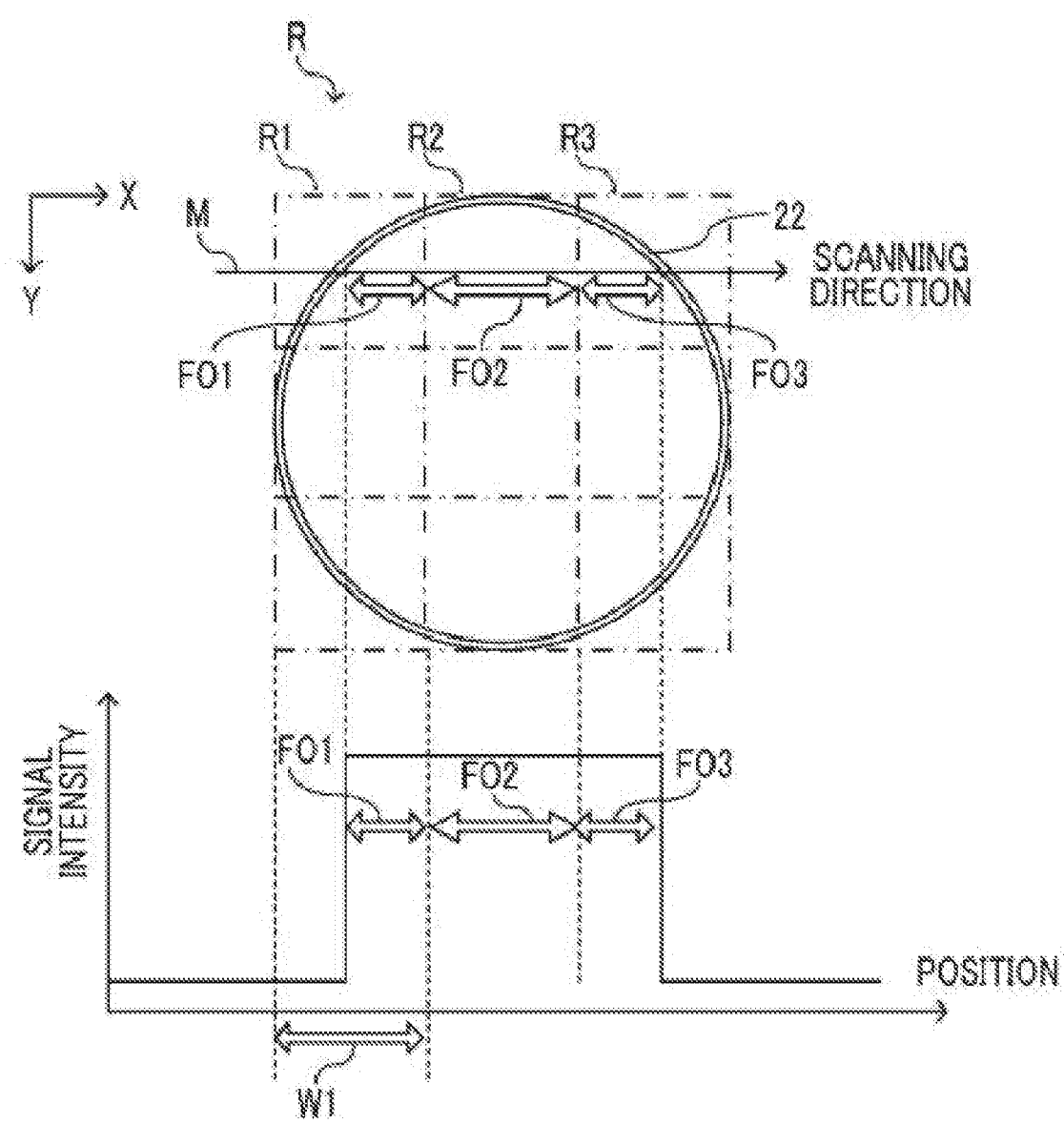
FIG. 7 is a diagram for describing a state where a measurement unit measures an accommodation part.

FIG. 4 is a diagram illustrating the scanning trajectory by a solid line M in the cultivation container. FIG. 5 and FIG. 6 are diagrams illustrating a positional relationship among the first displacement sensor, the second displacement sensor, and the cultivation container in a case where the field of view is present at any position in the cultivation container. FIG. 7 is a diagram for describing a state where the measurement unit measures the accommodation part.

In the present embodiment, the placing stand 10 is moved in the X direction and the Y direction under control of the scanning control unit 42, and the microscope device 30 two-dimensionally scans the inside of the cultivation container 20. During the scanning, partial images of the cultivation container 20 and the observation target are captured in each field of view of the microscope device 30. In the present embodiment, a well plate that includes six accommodation parts 22 is used as the cultivation container 20.

The microscope device control unit 41 reads out the imaging position and an imaging timing for imaging in each field of view R from the storage unit 44 and causes the microscope device 30 to image the inside of the cultivation container 20 in fields of view R1 to R54 as illustrated by surrounding dot-dashed lines in FIG. 4. Consequently, the field of view R of the microscope device 30 moves along the solid line M from a scanning start point S to a scanning end point E. That is, the field of view R is scanned in a positive direction (a rightward direction in FIG. 4) of the X direction and then, moves in the Y direction (a downward direction in FIG. 4) and is scanned in the opposite negative direction (a leftward direction in FIG. 4) of the X direction. Next, the field of view R moves in the Y direction again and is scanned in the positive direction of the X direction again. By repeating reciprocation of the field of view R in the X direction and movement of the field of view R in the Y direction, the inside of the cultivation container 20 is two-dimensionally scanned in an order of the fields of view R1 to R54.

Before the microscope device 30 performs imaging in the field of view R, the measurement unit 38 detects the distance from the imaging unit 37 to the bottom surface of the accommodation part 22.

In the present embodiment, as illustrated in FIG. 5 and FIG. 6, the first displacement sensor 38a and the second displacement sensor 38b are arranged in the X direction with the image forming optical system C interposed therebetween. The field of view R of the image forming optical system C two-dimensionally scans the inside of the cultivation container 20 as described above. At this point, the Z-directional position of the cultivation container 20 is detected at a position that is further in a movement direction of the field of view R than a position of the field of view R of the image forming optical system C with respect to the cultivation container 20. Specifically, in a case where the field of view R is moving in an arrow direction (a rightward direction in FIG. 5) illustrated in FIG. 5, the distance from the imaging unit 37 to the bottom surface of the accommodation part 22 is detected by the first displacement sensor 38a that is further in the movement direction of the field of view R between the first displacement sensor 38a and the second displacement sensor 38b. In a case where the field of view R moves from the position illustrated in FIG. 5 to a position of the first displacement sensor 38a, the autofocus control is performed using the previously detected Z-directional positional information of the cultivation container 20, and the partial images are captured.

In a case where the field of view R is moving in an arrow direction (a leftward direction in FIG. 6) in FIG. 6, the distance from the imaging unit 37 to the bottom surface of the accommodation part 22 is detected by the second displacement sensor 38b that is further in the movement direction of the field of view R between the first displacement sensor 38a and the second displacement sensor 38b. In a case where the field of view R moves from the position illustrated in FIG. 6 to a position of the second displacement sensor 38b, the autofocus control is performed using the previously detected Z-directional positional information of the cultivation container 20, and the phase difference images are captured.

The detection of the cultivation container 20 using the first displacement sensor 38a and the detection of the cultivation container 20 using the second displacement sensor 38b are switched depending on the movement direction of the field of view R. Accordingly, the distance from the imaging unit 37 to the bottom surface of the accommodation part 22 at the position of the field of view R can be always acquired before the capturing of the phase difference images in the field of view R.

Based on the Z-directional positional information of the cultivation container 20 detected beforehand as described above, the microscope device control unit 41 performs the autofocus control by controlling driving of the focus adjustment mechanism 35. Specifically, a relationship between the distance from the imaging unit 37 to the bottom surface of the accommodation part 22 and a movement amount of the image forming optical system C in the optical axis direction is set in advance in the microscope device control unit 41. The microscope device control unit 41 obtains the movement amount of the image forming optical system C in the optical axis direction based on the input distance from the imaging unit 37 to the bottom surface of the accommodation part 22 and outputs a control signal corresponding to the movement amount to the focus adjustment mechanism 35. The focus adjustment mechanism 35 is driven based on the input control signal. Accordingly, a focal length is set by moving the phase difference lens in the optical axis direction, and the autofocus control corresponding to the Z-directional position of the cultivation container 20 is performed.

As the distance from the imaging unit 37 to the bottom surface of the accommodation part 22 for the autofocus control, for example, an average value of the distance from the imaging unit 37 to the bottom portion of the accommodation part 22 between distances measured by the first displacement sensor 38a or the second displacement sensor 38b from the imaging unit 37 to a bottom surface of the cultivation container 20 within the field of view R is used.

A state where the measurement unit 38 measures the Z-directional position will be described with focus on one accommodation part 22 (the accommodation part 22 in an upper left part in FIG. 4) of the cultivation container 20.

FIG. 7 is a diagram for describing a state where the measurement unit measures the accommodation part. In FIG. 7, a scanning trajectory M of the measurement unit 38 when the accommodation part 22 is seen in a plan view is illustrated in an upper part, and a measurement result of the measurement unit 38 in the scanning trajectory is illustrated in a lower part.

For example, the measurement of the distance from the imaging unit 37 to the bottom surface of the accommodation part 22 that is measured by the first displacement sensor 38a before the imaging of the field of view R1 is performed in a range that is the entire region of the field of view R1 in FIG. 7. However, in a case where all measurement values of the field of view R1 are used, a measurement value that is not related to the distance from the imaging unit 37 to the bottom surface of the accommodation part 22 is also included. Accordingly, in order to perform the autofocus control on the observation target in the accommodation part 22, it is necessary to use the measurement result in which the measurement value not related to the distance from the imaging unit 37 to the bottom surface of the accommodation part 22 is excluded. In other words, it is necessary to use a range (effective range) in which the measurement unit 38 can measure the distance to the bottom surface of the accommodation part 22. The effective range is illustrated by a bidirectional arrow FO1 in FIG. 7.

As is apparent from comparison between the fields of view R1 to R3, the effective range in which the distance to the bottom portion of the accommodation part 22 can be measured varies for each field of view R. The entire width of the field of view R2 in the scanning direction is set as an effective range FO2. However, only the second half of the field of view R1 in the scanning direction is set as the effective range FO1, and only the first half of the field of view R3 in the scanning direction is set as an effective range FO3.

An abnormal value may be included in a part of the measurement values within the effective range due to disturbance. For example, the disturbance may occur due to a scratch or the like on the bottom portion of the accommodation part 22. In a case where there is a scratch or the like on the bottom portion of the accommodation part 22, the laser light of the irradiation from the measurement unit 38 is subjected to diffuse reflection on the bottom portion of the accommodation part 22, and the measurement value may be obtained as an abnormal value in a case where accurate detection cannot be performed in the measurement unit 38.

In addition, for example, the disturbance may occur due to vibration. As a result of vibration, a distance from the measurement unit 38 to the bottom surface of the accommodation part 22 instantaneously changes. In a case where the distance at the moment is measured by the measurement unit 38, the measurement value is obtained as an abnormal value. In a case where an effect of the abnormal value is strong, consequently, the autofocus control cannot be appropriately performed. In a case where a distance of the effective range in the scanning direction in the field of view R as a target is sufficiently long, the effect of the abnormal value is weak even in a case where the abnormal value is included in a part of the measurement values within the effective range due to the disturbance. By averaging the measurement result using only the measurement result within the effective range, the distance from the imaging unit 37 to the bottom surface of the accommodation part 22 for the autofocus control can be obtained. However, in a case where the distance of the effective range in the scanning direction in the field of view R as a target of the autofocus control is not sufficient, the effect of the abnormal value is strong in a case where the abnormal value is included in a part of the measurement values within the effective range due to the disturbance, and an appropriate value is not obtained when the distance from the imaging unit 37 to the bottom surface of the cultivation container 20 is obtained by averaging the measurement value within the effective range. Consequently, the autofocus control cannot be appropriately performed. The effect of the abnormal value is increased.

In order to prevent such a case, the observation apparatus of the present embodiment measures the distance to the bottom surface of the accommodation part 22 in a sufficient effective range in any field of view R and performs imaging by appropriate autofocus control. Hereinafter, an observation method of the observation apparatus will be described. An algorithm illustrated below is implemented by causing the CPU to execute the program stored in the storage unit 44.

Figure 8:
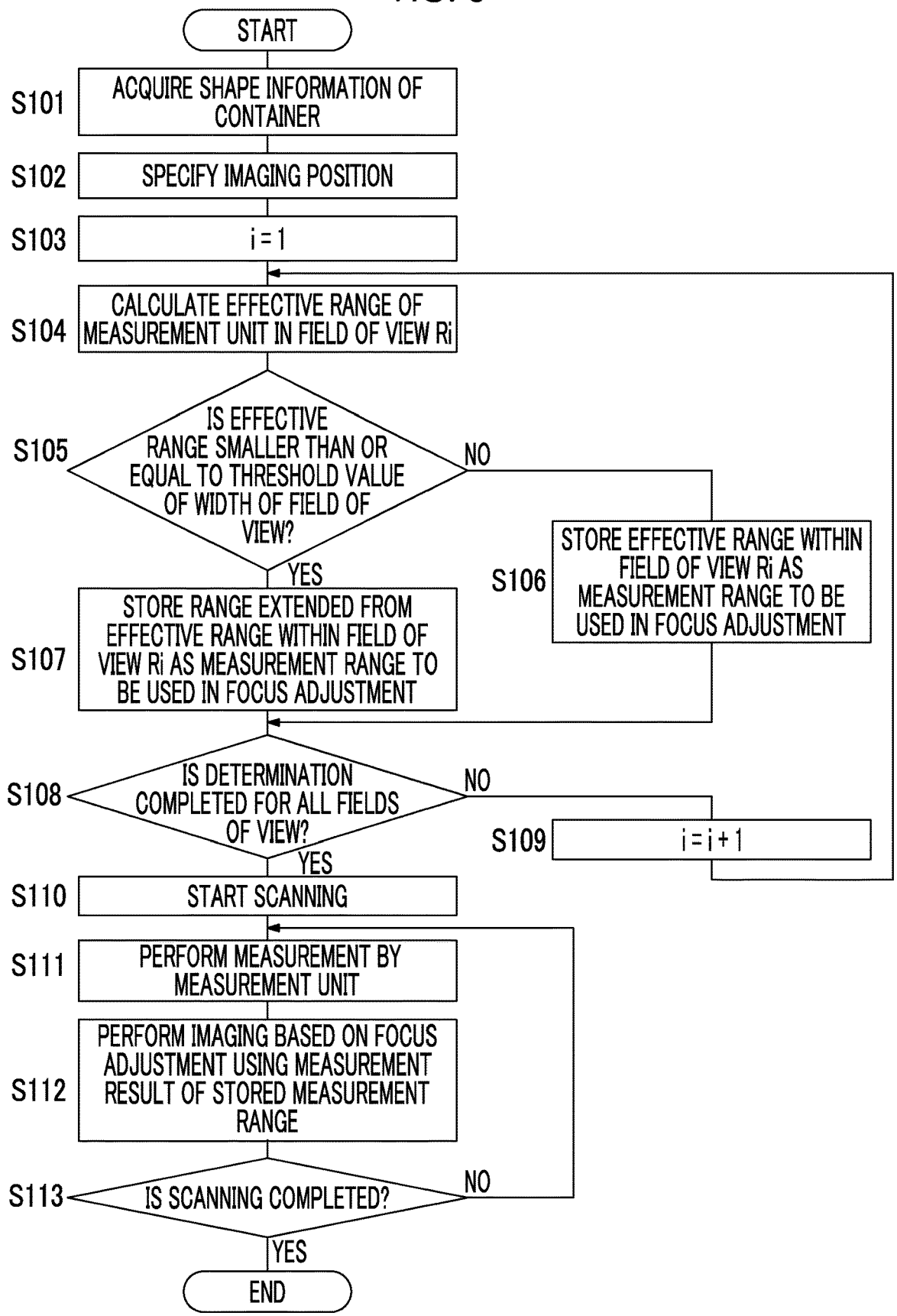
FIG. 8 is a flowchart illustrating a flow of observation method executed by the observation apparatus.
Figure 9:
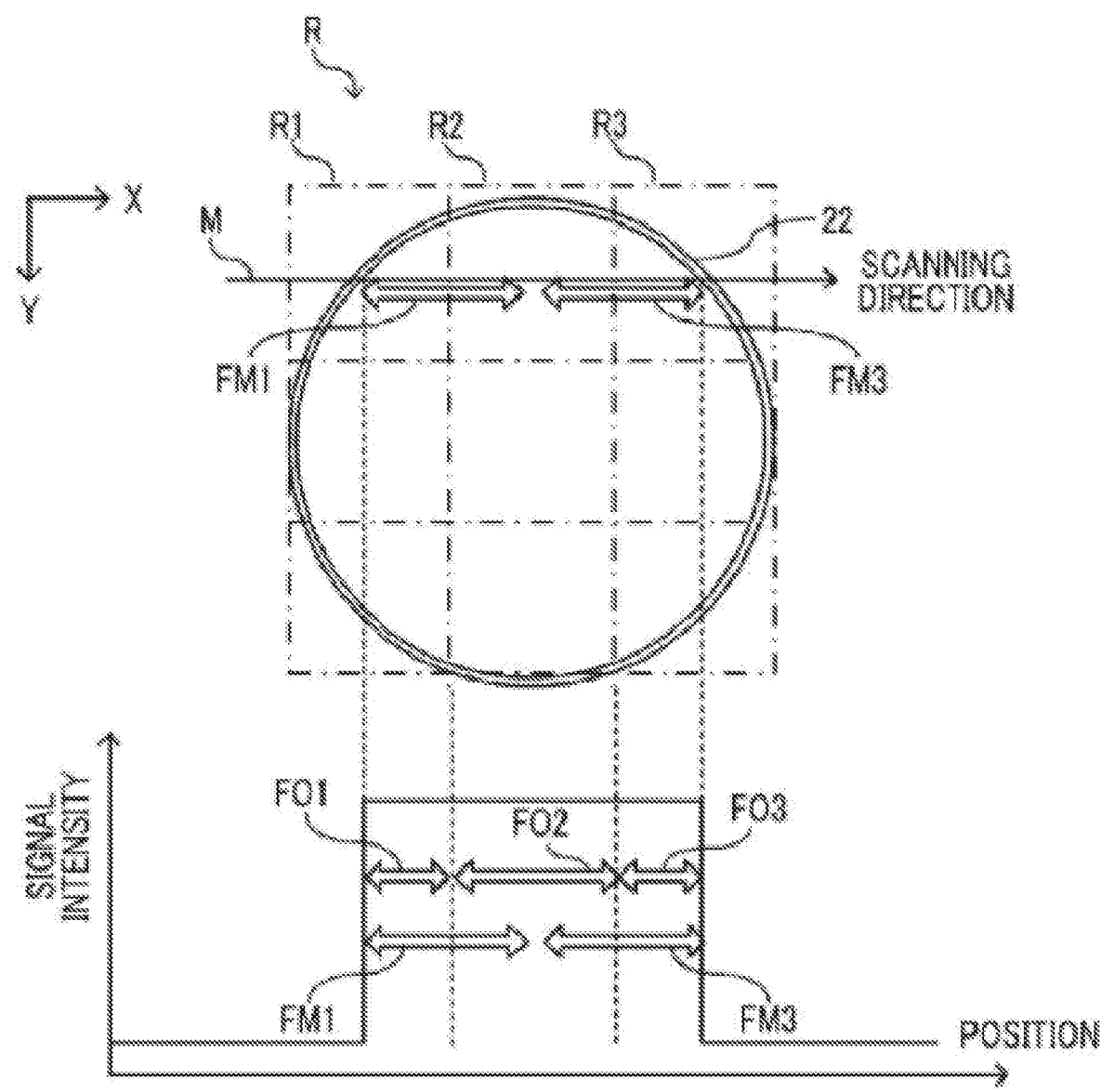
FIG. 9 is a diagram illustrating an example in which a range extended from an effective range within the field of view is set as a range in which a measurement result of the measurement unit is used for autofocus control.

FIG. 8 is a flowchart illustrating a flow of observation method executed by the observation apparatus. Each step is executed by the control unit 40. FIG. 9 is a diagram illustrating an example in which a range extended from the effective range within the field of view is set as a range in which the measurement result of the measurement unit is used for the autofocus control.

First, the control unit 40 receives an input of the container information of the cultivation container 20 from the user in the input unit 46 and acquires the shape information of the cultivation container 20 stored in the storage unit 44 based on the input container information of the cultivation container 20 (step S101). Information of the number of accommodation parts 22 of the currently used cultivation container 20, the intervals of the accommodation parts 22, the diameter of the accommodation part 22, and the like is obtained from the shape information.

Next, the control unit 40 specifies the imaging positions from the shape information of the cultivation container 20 obtained in step S101 (step S102). The imaging positions are specified as coordinate positions of the X-Y plane of the placing stand 10 at which the observation target accommodated in the cultivation container 20 can be observed. For example, the control unit 40 specifies XY coordinates of the image forming optical system C for performing imaging in the field of view R1 to the field of view R54 illustrated in FIG. 4 as the imaging positions by assuming a state where the cultivation container 20 of which the shape is specified in step S101 is appropriately placed on the placing stand 10. In addition, the control unit 40 specifies a trajectory connecting the imaging positions as the scanning trajectory M. The control unit 40 may first decide the scanning trajectory based on the shape information of the cultivation container 20 and specify the coordinates of the imaging positions on the scanning trajectory. The scanning trajectory is preferably configured with straight lines as far as possible except for a time when the direction is changed.

Next, the control unit 40 substitutes i with 1 as an initial value in all fields of view Ri (i=1 to 54) in order to perform a subsequent process (step S103).

The control unit 40 calculates the effective range information indicating the effective range of the measurement unit 38 in the field of view Ri (step S104).

The control unit 40 determines whether or not the effective range of the measurement unit 38 in the field of view Ri is smaller than or equal to a predetermined threshold value (step S105). The threshold value is a value that can be randomly decided by the user, and is a value that indicates a length so as to be compared with the effective range. For example, the threshold value is set to a length of a range in which desired accuracy is secured even with the disturbance as a scanning range in which the measurement unit 38 measures the distance from the imaging unit 37 to the bottom surface of the accommodation part 22. In the present embodiment, the threshold value is described as half of a width of the field of view Ri of the imaging unit 37 along the scanning trajectory. However, as described above, the threshold value can be randomly decided by the user considering measurement accuracy and is not limited to half of the width of the field of view Ri. In a case of the field of view R1 in FIG. 9, the control unit 40 determines that the effective range FO1 is smaller than or equal to half of the width of the field of view in the scanning direction. In a case of the field of view R2 in FIG. 9, the control unit 40 determines that the effective range FO2 is larger than half of the width of the field of view in the scanning direction.

In a case where the effective range is not smaller than or equal to half of the width of the field of view (step S105: NO), the control unit 40 stores only the effective range within the field of view Ri in the storage unit 44 as the effective range in which the measurement result of the measurement unit 38 is used for the autofocus control (step S106). The reason is that a size of the effective range is regarded as a sufficient size for use in the autofocus control in the present embodiment.

In a case where the effective range is smaller than or equal to half of the width of the field of view (step S105: YES), the control unit 40 stores not only the effective range within the field of view Ri but also a range extended from the effective range within the field of view Ri in the storage unit 44 as a measurement range in which the measurement result of the measurement unit 38 is used for the autofocus control (step S107). The reason is that the size of the effective range is insufficient for use in the autofocus control.

As a specific example of a method of extending the effective range, the control unit 40 stores the effective range and a range extended to the field of view Ri+1 or the field of view Ri−1 adjacent to the field of view Ri in the storage unit 44 as the measurement range. For example, in the case of the field of view R1 in FIG. 9, the distance from the imaging unit 37 to the bottom surface of the accommodation part 22 can be sufficiently measured by the measurement unit 38 in the adjacent field of view R2. Therefore, the control unit 40 sets an effective range FM1 extended from the effective range FO1 within the field of view R1 to the inside of the field of view R2 as the effective range to be used in the autofocus control in a case where the field of view R1 is imaged by the microscope device 30. Accordingly, as illustrated in the lower part of FIG. 9, the measurement result of the measurement unit 38 in the extended effective range FM1 is averaged and is used in the autofocus control of the field of view R1. As illustrated in FIG. 9, the extended effective range FM1 preferably includes the effective range FO1 and the measurement range within the field of view R2 that is contiguous with the effective range FO1. For example, the extended effective range FM1 is set to be equal to the length of the threshold value. In this case, the effective range of the adjacent field of view R2 is included to an extent of an insufficient length of the effective range FO1 with respect to half of the width of the field of view, which is the threshold value, and the extended effective range FM1 is obtained. Alternatively, the extended effective range FM1 may be set to be larger than or equal to the threshold value (half of the field of view R) and smaller than or equal to the entire length of the field of view R.

In addition, for example, in a case of the field of view R3 in FIG. 9, the distance from the imaging unit 37 to the bottom surface of the accommodation part 22 can be sufficiently measured by the measurement unit 38 in the adjacent field of view R2. The control unit 40 sets an effective range FM3 extended from the effective range FO3 within the field of view R3 to the inside of the field of view R2 as the measurement range to be used in the autofocus control in a case where the field of view R3 is imaged by the microscope device 30. Accordingly, as illustrated in the lower part of FIG. 9, the measurement result of the measurement unit 38 in the extended effective ranges FM1 and FM3 is averaged and is used in the autofocus control of the field of view R1 and the field of view R3.

Next, the control unit 40 determines whether or not the determination of the effective range is completed for all fields of view (step S108). In a case where the determination for all fields of view is not finished (step S108: NO), the control unit 40 repeats the process from step S104 by increasing i by 1 (step S109). In a case where the determination for all fields of view is finished (step S108: YES), the control unit 40 starts scanning the cultivation container 20 by starting imaging by the microscope device 30 while causing the scanning control unit 42 to move the placing stand 10 along the scanning trajectory (step S110).

The control unit 40 measures the distance from the imaging unit 37 to the bottom surface of the accommodation part 22 by the measurement unit 38 before imaging and stores the distance in the storage unit 44 (step S111).

The control unit 40 averages the measurement result of the measurement unit 38 in the effective range stored in step S106 or step S107 and uses the measurement result in the autofocus control, and performs imaging by the microscope device 30 at the imaging position in each field of view (step S112).

The control unit 40 determines whether or not the scanning is completed, that is, whether or not the imaging is finished at all imaging positions (step S113). In a case where the scanning is not completed (step S113: NO), a return is made to the process of step S111, and the measurement by the measurement unit 38 and subsequent imaging are performed. In a case where the scanning is completed (step S113: YES), the control unit 40 finishes an observation process.

As described thus far, even in a case where the effective range of the measurement unit 38 in the field of view R, that is, the length of the accommodation part 22 included in the field of view R along the scanning trajectory, is smaller than or equal to the threshold value (half of the width of the field of view), the observation apparatus of the embodiment uses the measurement result of the measurement unit 38 by setting the effective range extended to the effective range of the adjacent field of view. Accordingly, even in a case where the disturbance such as vibration occurs, the effect of the disturbance can be decreased compared to the effect of the disturbance in a case where the autofocus control is performed using the measurement result of only the effective range of the field of view R which is the target of the autofocus control. In other words, the observation apparatus can capture an image by appropriately performing the autofocus control regardless of the size of the effective range in which the distance to the accommodation part of the cultivation container 20 can be measured within the field of view R.

In the embodiment, the imaging performed by the microscope device 30 is started after the completion of the determination of the effective range for all fields of view. However, the imaging is not for limitation purposes. The determination of the effective range of each field of view may be performed in parallel with the imaging performed by the microscope device 30.

The observation process that is executed by causing the CPU to read software (program) in the embodiment may be executed by various processors other than the CPU. In this case, the processors are illustrated by a programmable logic device (PLD) such as a field-programmable gate array (FPGA) of which a circuit configuration can be changed after manufacturing, a dedicated electric circuit such as an application specific integrated circuit (ASIC) that is a processor having a circuit configuration dedicatedly designed to execute a specific process, and the like. In addition, the observation process may be executed by one of the various processors or may be executed by a combination of two or more processors of the same type or different types (for example, a plurality of FPGAs and a combination of a CPU and an FPGA). In addition, a hardware structure of the various processors is more specifically an electric circuit in which circuit elements such as semiconductor elements are combined.

In the embodiment, an aspect in which the program of the observation process is stored (installed) in advance in the storage unit 44 is described. However, the aspect is not for limitation purposes. The program may be provided in a form of a recording on a recording medium such as a compact disk read only memory (CD-ROM), a digital versatile disk read only memory (DVD-ROM), and a Universal Serial Bus (USB) memory. In addition, the program may be downloaded from an external device through a network.

EXPLANATION OF REFERENCES

10: placing stand
11: opening
12: movement unit
20: cultivation container
21: plate
22: accommodation part
30: microscope device
31: light source
32: slit
33: condenser lens
34: objective lens
35: focus adjustment mechanism
36: image forming lens
37: imaging unit
38: measurement unit
38*a*: first displacement sensor
38*b*: second displacement sensor
40: control unit
41: microscope device control unit
42: scanning control unit
43: display control unit
44: storage unit
45: calculation unit
46: input unit
47: display unit
C: image forming optical system
E: scanning end point
FO1 to FO3: effective range
FM1, FM3: extended range
L: illumination light
M: scanning trajectory
R, R1 to R54: field of view
S: scanning start point

What is claimed is:

1. An observation apparatus comprising:
    an imaging unit that images an observation target accommodated in an accommodation part of a container in a field of view smaller than the accommodation part at a series of predetermined imaging positions and acquires a series of partial images;
    a measurement unit that measures a distance from the imaging unit to the accommodation part before each imaging performed by the imaging unit at the series of imaging positions;
    a storage unit that stores shape information representing a shape of the container and imaging position information representing the series of imaging positions;
    a calculation unit that calculates effective range information indicating an effective range based on the shape information and the imaging position information, the effective range being a range in which the distance is measurable by the measurement unit before imaging within a range of the field of view of the imaging unit at the imaging positions; and
    a control unit that compares the effective range with a predetermined threshold value based on the effective range information and controls a focus of imaging using a measurement result measured by the measurement unit in the effective range and a measurement result of the measurement unit in a field of view adjacent to the field of view including the effective range in a case where the effective range is smaller than or equal to the threshold value.

2. The observation apparatus according to claim 1,
    wherein in a case where the effective range is smaller than or equal to the threshold value, the control unit uses the measurement result of the measurement unit in the adjacent field of view in a larger range as the effective range is smaller.

3. The observation apparatus according to claim 1,
    wherein the threshold value is a length of half of a width of the field of view of the imaging unit.

4. The observation apparatus according to any one of claim 1,
    wherein in a case where the effective range is smaller than or equal to the threshold value, the control unit controls the focus using the measurement result of the measurement unit in the adjacent field of view to an extent of an insufficient length of the effective range with respect to the threshold value.

5. An observation method comprising:
- a measurement step of, in a case where an observation target accommodated in an accommodation part of a container is imaged by an imaging unit having a field of view smaller than the accommodation part at a series of predetermined imaging positions and a series of partial images are acquired, measuring a distance from the imaging unit to the accommodation part before acquisition of each of the series of partial images;
- a storage step of storing shape information representing a shape of the container and imaging position information representing the series of imaging positions;
- a calculation step of calculating effective range information indicating an effective range based on the shape information and the imaging position information, the effective range being a range in which the distance is measurable in the measurement step before imaging within a range of the field of view at the imaging positions; and
- a control step of comparing the effective range with a predetermined threshold value based on the effective range information calculated in the calculation step and controlling a focus of imaging using a measurement result measured in the measurement step in the effective range and a measurement result of the measurement step in a field of view adjacent to the field of view including the effective range in a case where the effective range is smaller than or equal to the threshold value.

* * * * *